United States Patent
Lowe

(10) Patent No.: US 8,267,861 B2
(45) Date of Patent: Sep. 18, 2012

(54) DISPOSABLE MOUTH PROPS

(76) Inventor: Richard D. Lowe, Brea, CA (US)

( * ) Notice: Subject to any disclaimer, the term of this patent is extended or adjusted under 35 U.S.C. 154(b) by 1015 days.

(21) Appl. No.: 11/890,171

(22) Filed: Aug. 3, 2007

(65) Prior Publication Data

US 2008/0038689 A1 Feb. 14, 2008

Related U.S. Application Data

(60) Provisional application No. 60/836,113, filed on Aug. 8, 2006.

(51) Int. Cl.
*A61B 1/32* (2006.01)
(52) U.S. Cl. ........................................................ 600/238
(58) Field of Classification Search .......... 600/237–244; 433/93, 140
See application file for complete search history.

(56) References Cited

U.S. PATENT DOCUMENTS

| | | | |
|---|---|---|---|
| 264,260 A * | 9/1882 | Donaldson | 600/238 |
| 323,627 A * | 8/1885 | Bickford | 600/238 |
| 410,665 A * | 9/1889 | Daintree | 600/238 |
| 606,781 A * | 7/1898 | Halperin | 600/238 |
| 1,415,347 A * | 5/1922 | Heidbrink | 600/238 |
| 2,172,998 A * | 9/1939 | Grout et al. | 601/139 |
| 4,585,416 A * | 4/1986 | DeNiro et al. | 433/140 |
| 4,802,851 A * | 2/1989 | Rhoades | 433/93 |
| 5,347,996 A * | 9/1994 | Huan | 600/238 |
| 5,924,866 A * | 7/1999 | Eldreth | 433/140 |
| 2003/0039942 A1* | 2/2003 | Phillips | 433/140 |
| 2003/0082495 A1* | 5/2003 | Fischer | 433/140 |

* cited by examiner

*Primary Examiner* — Eduardo C Robert
*Assistant Examiner* — Jerry Cumberledge
(74) *Attorney, Agent, or Firm* — Sandy Lipkin

(57) ABSTRACT

An improved dental prop that is formed of a slim, cylindrical configuration for bilateral access with voided areas on either end for the purpose of aiding in the comfort of the patient by allowing the patient's jaw to relax during lengthy dental procedures, while effectively articulating the mouth in an open position. The prop contains a safety line eyelet, perpendicular to the center of the cylindrical body, thereby allowing a dentist an extra precautionary step toward the safety of the patient in the case of ingestion or aspiration.

2 Claims, 1 Drawing Sheet

U.S. Patent
Sep. 18, 2012
US 8,267,861 B2
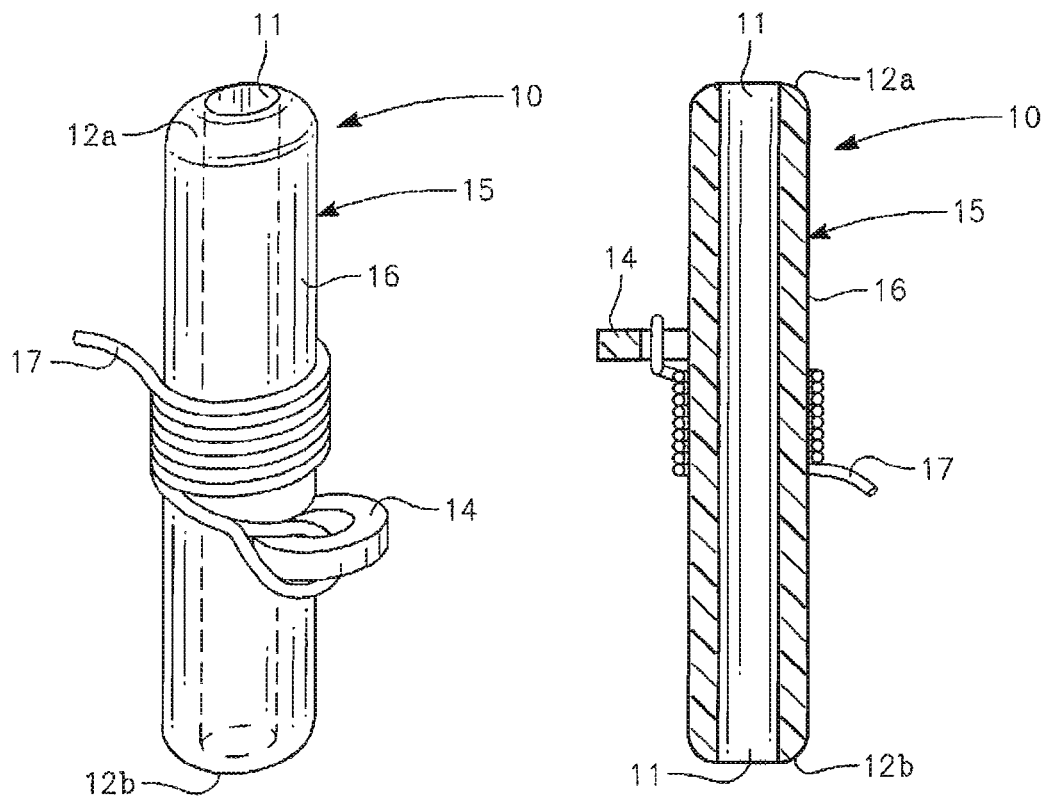
FIG. 1
FIG. 2
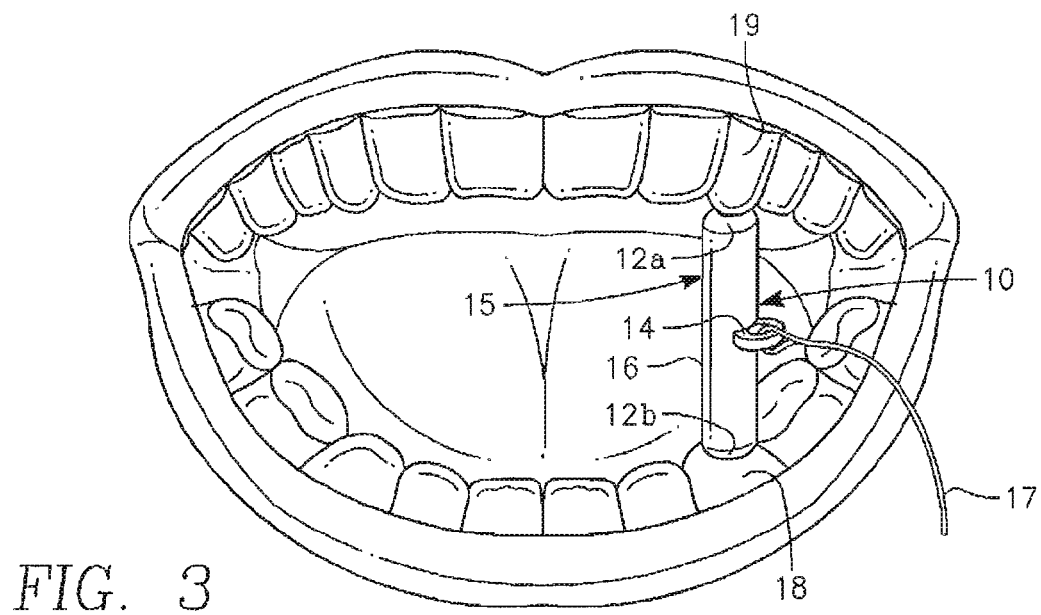
FIG. 3

DISPOSABLE MOUTH PROPS

REFERENCE TO PRIOR APPLICATION

This application claims the priority of provisional application 60/836,113, filed Aug. 8, 2006 entitled MINI-PROP by Richard D. Lowe.

BACKGROUND OF THE INVENTION

1. Field of the Invention

The present invention relates generally to the field of dental tools, and particularly toward a device that allows dentists and registered dental assistants ("RDA's") easy bilateral visualization and accessibility to the inside of a patient's mouth.

2. Description of the Prior Art

Dental props are devices that are inserted into a patient's mouth between the upper and lower teeth in order to keep the mouth opened in a fixed position while the dentist is working in the patient's mouth. Normally, the teeth on one side of the mouth engage the dental prop while the dentist is working on the teeth on the opposite side of the mouth. Dental props are desirable, particularly in order to enhance the efficiency of the dentist, so the dentist does not have to continually remind the patient to keep his or her mouth open at a certain angle and also so that the dentist does not have to be concerned with the patient inadvertently biting his or her fingers or the dental instruments.

Dental props have been devised with many shapes and configurations, but heretofore no dental prop has been devised that is simple in design that allows for bilateral visualization and accessibility into the patient's mouth when wand instruments, such as suction devices, etc. are utilized.

Accordingly, the device of the instant invention provides for a new, improved, streamlined, versatile dental prop.

SUMMARY OF THE INVENTION

The preferred embodiment of the present invention teaches a dental prop comprising a main body portion, with the main body portion having a peripheral wall, a first end and a second end that defines a hollow interior portion therein and an aperture in the first end that extends through the hollow interior portion and terminates in an aperture at the second end.

The above embodiment can be further modified by defining that there is an eyelet positioned on the peripheral wall in a position substantially perpendicular to the main body portion.

BRIEF DESCRIPTION OF THE DRAWINGS

FIG. 1 is a perspective view of the invention.
FIG. 2 is a side view of the invention.
FIG. 3 is a view of the invention in the mouth of a patient.

DETAILED DESCRIPTION OF A PREFERRED EMBODIMENT

Turning to the drawings, the preferred embodiment is illustrated and described by reference characters that denote similar elements throughout the several views of the instant invention.

The dental prop 10 is a slim, cylindrical device with a voided interior that terminates in apertures 11 located on either end 12a, 12b of the body 16. It is designed for the purpose of aiding in the comfort of the patient by allowing the patient's jaw to relax during lengthy dental procedures, while effectively articulating the mouth in an open position, as seen in FIG. 3.

The slim, cylindrical design is accommodating to dentists and registered dental assistants ("RDAs"), by allowing bilateral visualization and accessibility when wand instruments, such as suction devices, are necessary. There is a safety line eyelet 14, placed perpendicular to the center 15 of the cylindrical body 16, thereby allowing the dentist an extra precautionary step toward the safety of the patient in the case of ingestion or aspiration by the attachment of floss 17 through the eyelet 14.

The prop 10 is designed to optimally positioned directly over the lower cuspid (tip) 18. A portion of the tooth (approximately 1/16") would then fit securely in the voided area of the chosen end. Then the patient, with the devise held in the vertical position, can relax his or her jaw, allowing approximately 1/16" of the upper cuspid tip 19 to fit securely in the voided area at the available end.

Typically, the prop 10 is 1 3/8" in length, 1/4" outer diameter and 1/8" inner diameter. The safety half-loop/eyelet 14 is 3/16" in width and perpendicular to the center 15 of the body 16, 3/16" in length and 1/16" inner diameter.

The illustrations and examples provided herein are for explanatory purposes and are not intended to limit the scope of the appended claims. This disclosure is to be considered an exemplification of the principles of the invention and is not intended to limit the spirit and scope of the invention and/or claims of the embodiment illustrated. Those skilled in the art will make modifications to the invention for particular applications of the invention.

What is claimed is:

1. A dental prop consisting of
   a cylindrical main body portion, said main body portion having a peripheral wall, a first end and a second end defining an interior portion extending from said first end through said second end wherein said main body portion maintains its shape under pressure from both said first end and said second end without the aid of supporting elements when said first end and said second end are placed between the jaws of a human mouth;
   an aperture at said first end;
   and an aperture at said second end wherein a safety eyelet is positioned on said peripheral wall in a position substantially perpendicular to said main body portion for placement therein of tethering material.

2. A method of propping open a human mouth to conduct dental work therein comprising the steps of:
   obtaining a dental prop, said dental prop consisting of:
   a cylindrical main body portion, said main body portion having a peripheral wall, a first end and a second end defining an interior portion extending from said first end through said second end wherein said main body portion maintains its shape under pressure from both said first end and said second end without the aid of supporting elements when said first end and said second end are placed between the jaws of a human mouth;
   an aperture at said first end;
   and an aperture at said second end wherein a safety eyelet is positioned on said peripheral wall in a position substantially perpendicular to said main body portion for placement therein of tethering material;

placing said aperture at said first end to one of said human's upper teeth;

placing said aperture at said second end to one of said humans' lower teeth wherein said one of said human's upper teeth is in general alignment with said one of said human's lower teeth; and placement of a tethering material, through said eyelet to act as an anchor to said prop should said human be in danger of swallowing said dental prop.

\* \* \* \* \*